United States Patent
Merz et al.

(10) Patent No.: US 10,532,162 B2
(45) Date of Patent: Jan. 14, 2020

(54) METHOD AND DEVICE FOR DETERMINING AN INJECTION PROCESS OF AN INJECTION APPLIANCE, AND INJECTION APPLIANCE FOR INJECTING FLUID

(71) Applicant: Robert Bosch GmbH, Stuttgart (DE)

(72) Inventors: Andreas Merz, Freiberg am Neckar (DE); Fabian Utermoehlen, Leonberg (DE); Michael Stumber, Korntal-Muenchingen (DE); Stefan Leidich, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 344 days.

(21) Appl. No.: 15/598,364

(22) Filed: May 18, 2017

(65) Prior Publication Data
US 2017/0333637 A1   Nov. 23, 2017

(30) Foreign Application Priority Data
May 19, 2016   (DE) .................. 10 2016 208 635

(51) Int. Cl.
*G01D 5/20* (2006.01)
*A61M 5/315* (2006.01)
*A61M 5/28* (2006.01)

(52) U.S. Cl.
CPC .......... *A61M 5/31568* (2013.01); *A61M 5/28* (2013.01); *A61M 5/31528* (2013.01);
(Continued)

(58) Field of Classification Search
CPC .... A61M 5/16831; A61M 3/00; A61M 3/005; A61M 5/322; A61B 5/05; A61B 5/14503; G01R 3/00; A61J 1/00
See application file for complete search history.

(56) References Cited

U.S. PATENT DOCUMENTS 3,715,919 A * 2/1973 Kishimoto .............. G01F 1/582
                                                73/861.11
4,478,713 A * 10/1984 Girot ...................... B01D 15/08
                                                210/101
(Continued)

FOREIGN PATENT DOCUMENTS

DE           41 23 781 A1    1/1993
DE   10 2004 063 644 A1    7/2006
(Continued)

*Primary Examiner* — Alesa Allgood
(74) *Attorney, Agent, or Firm* — Maginot, Moore & Beck LLP (57) ABSTRACT

A method for determining an injection process of an injection appliance includes injecting a fluid with the injection appliance and applying an electrical signal to at least one helical spring of the injection appliance coupled to a dosing wheel of the injection appliance. The method also comprises detecting an inductance value of the at least one helical spring. A number of windings of the at least one helical spring is dependent on a set rotation angle of the dosing wheel. The set rotation angle corresponds to a dose quantity of the fluid that is preselected for the injection process. The method moreover includes making available a determination signal representing the determined injection process, using the detected inductance value.

5 Claims, 4 Drawing Sheets

(52) U.S. Cl.
CPC ... *G01D 5/2006* (2013.01); *A61M 2205/3306* (2013.01); *A61M 2205/3317* (2013.01); *A61M 2205/3584* (2013.01); *A61M 2205/50* (2013.01); *A61M 2205/702* (2013.01)

(56) References Cited

U.S. PATENT DOCUMENTS

| | | | | |
|---|---|---|---|---|
| 7,779,835 | B2* | 8/2010 | Hamano | A61M 15/025 128/200.23 |
| 8,240,303 | B2* | 8/2012 | Hamano | A61M 15/025 128/200.23 |
| 9,714,877 | B2* | 7/2017 | Nakamura | G01L 3/103 |
| 9,987,425 | B2* | 6/2018 | Alderete | F04B 19/22 |
| 10,010,668 | B2* | 7/2018 | Tieck | F04B 9/042 |
| 2016/0367750 | A1* | 12/2016 | Tieck | F04B 9/042 |
| 2016/0367751 | A1* | 12/2016 | Bazargan | A61M 5/14216 |
| 2016/0367754 | A1* | 12/2016 | Alderete, Jr. | A61M 5/16831 |
| 2016/0369789 | A1* | 12/2016 | Alderete, Jr. | F04B 19/22 |
| 2016/0369790 | A1* | 12/2016 | Yavorsky | F04B 51/00 |
| 2017/0032152 | A1* | 2/2017 | Salem | G06K 19/077 |

FOREIGN PATENT DOCUMENTS

| | | |
|---|---|---|
| DE | 10 2009 003 721 A1 | 10/2010 |
| EP | 1 095 668 A1 | 5/2001 |

\* cited by examiner

METHOD AND DEVICE FOR DETERMINING AN INJECTION PROCESS OF AN INJECTION APPLIANCE, AND INJECTION APPLIANCE FOR INJECTING FLUID

This application claims priority under 35 U.S.C. § 119 to patent application no. DE 10 2016 208 635.9, filed on May 19, 2016 in Germany, the disclosure of which is incorporated herein by reference in its entirety.

BACKGROUND

The disclosure proceeds from a device or a method of the type according to the independent claims. The present disclosure also relates to a computer program.

For example, a deficiency of endogenous insulin in diabetes mellitus can be treated by injection of an insulin preparation. In customary injection methods, the injection appliances used can include disposable syringes, permanent insulin pumps, or disposable or multi-use insulin pens.

DE 10 2009 003 721 A1 describes an arrangement for administering insulin or other medicaments from a carpule.

SUMMARY

Against this background, the present disclosure proposes a method, furthermore a device that uses this method, an injection appliance with the device, and, finally, a corresponding computer program, in accordance with the main claims. Advantageous developments and improvements of the device set out in the independent claim are possible by means of the measures set out in the dependent claims.

According to embodiments, an injection process can be permitted in particular by means of an injection appliance, for example an insulin pen, with a dose sensor system based on a spring functioning as a coil and having a variable number of windings. A method, a device and an injection appliance can in particular be made available, wherein a spring is used, which is rotated about a rotation angle dependent on a set dose of a fluid and whose potential energy can be converted into a translation movement during the injection process, so that, by measuring an inductance of the spring, it is possible to draw conclusions regarding a dosed quantity of the peace. For example, data concerning the injection process can be stored and displayed.

Advantageously, according to embodiments, it is possible in particular to increase the safety of a person using the injection appliance, for example since a correct dose of fluid or a correct quantity of insulin can be permitted. Moreover, for example, an outer form of an already available injection appliance does not need to be modified, or appreciably modified, and an inner structure of an injection appliance can be realized with minimal modifications in relation to existing injection appliances. Thus, cost-effective determination of an injection process can be permitted in particular, since at least some of the already existing components of an injection appliance can be used. Moreover, for example, an uncomplicated evaluation of inductive signals can be used to determine the injection process. Moreover, particularly in the healthcare sector, administration work in respect of documentation of injections can be minimized, for example since a handwritten record for a physician can be dispensed with and, instead, an automatically detected dose value and the like can be documented electronically, for example also in an application on a mobile appliance, and can be forwarded electronically.

A method for determining an injection process of an injection appliance is proposed, wherein a fluid is injectable by means of the injection appliance, wherein the method comprises the following steps:

an electrical signal is applied to at least one helical spring of the injection appliance, which helical spring is coupled to a dosing wheel of the injection appliance;

an inductance value of the at least one helical spring is detected, wherein a number of windings of the at least one helical spring is dependent on a set rotation angle of the dosing wheel, wherein the set rotation angle corresponds to a dose quantity of the fluid that is preselected for the injection process; and a determination signal which represents the determined injection process is supplied using the detected inductance value.

This method can be implemented, for example, in software or hardware, or in a combined form of software and hardware, for example in a control system or a device. In this case, an injection process can be determined in particular quantitatively and, in addition or alternatively, based on time. The injection appliance can be designed, for example, as an insulin pen for injecting an insulin solution. Such an insulin pen can in particular be designed similarly to a thick ballpoint pen and can be equipped with an insulin carpule. A carpule can be understood as a cylindrical ampule which can be provided at one end with a pierceable membrane, while the other end can be closed with a displaceable stopper. By means of the dosing wheel, which can also be designated as a dosing knob, a required or desired dose or amount of fluid can be set or preselected for the injection process by rotating the dosing wheel about a rotation angle. The injection appliance can in this case be an injection appliance with a rotatably configured dosing wheel which executes a rotation only during dose setting.

According to one embodiment, the method can comprise a step in which the dose quantity of the fluid is calculated or determined using the detected inductance value. In addition or alternatively, the method can comprise a step in which the detected inductance value or the calculated dose quantity is combined with a time stamp which represents a time point of the injection process. In this step, a determination signal can be supplied which represents the calculated dose quantity and, in addition or alternatively, the time point of the injection process. Such an embodiment affords the advantage that an injection process can be determined in an exact, meaningful and reliable manner.

The method can also comprise a step in which the determination signal is output to an interface to a transmission device for transmitting the determination signal to an appliance outside the injection appliance, to an interface to a memory inside or outside the injection appliance, and, in addition or alternatively, to an interface to a display device of the injection appliance. Such an embodiment affords the advantage that user comfort and the safety of use of the injection appliance can be enhanced, since information can be made available concerning an injection process.

Moreover, in the step of applying an electrical signal, an alternating electrical signal can be applied to the at least one helical spring. In the detection step, in this case, the inductance value of the at least one helical spring can be detected using a resonant frequency of an electrical detection circuit connected to the at least one helical spring, an electrical voltage of a capacitor of an electrical detection circuit connected to the at least one helical spring, an electrical shunt resistance of an electrical detection circuit connected to the at least one helical spring, and, in addition or alternatively, a phase relationship between the applied electrical signal and a voltage across an electrical detection circuit connected to the at least one helical spring. Alternatively, in the step of applying an electrical signal, a constant electrical signal can be applied to the at least one helical spring. In the detection step, in this case, the inductance value of the at least one helical spring can be detected using a change, converted to a measurement voltage, of an electrical current in an electrical detection circuit connected to the at least one helical spring. Such an embodiment affords the advantage that the inductance value can be detected safely, inexpensively and exactly, wherein, in respect of a detection principle, special application fields or embodiments of the injection appliance can also be taken into consideration.

The approach proposed here also make available a device designed to perform and control the steps of a variant of a method proposed here in corresponding devices. The object of the disclosure can also be achieved quickly and efficiently with this embodiment variant of the disclosure in the form of a device.

In this connection, the device can comprise at least one computation unit for processing signals or data, at least one memory for storing signals or data, at least one interface to a sensor or to an actuator for reading in sensor signals from the sensor or for outputting data or control signals to the actuator, and/or at least one communication interface for reading in or outputting data which are embedded in a communications protocol. The computation unit can be, for example, a signal processor, a microcontroller or the like, wherein the memory can be a flash memory, an EPROM or a magnetic storage unit. The communication interface can be designed to read in or output data wirelessly and/or by wire, wherein a communication interface that can read in or output wired data is able to read in these data for example electrically or optically from a corresponding data transmission line or can output same into a corresponding data transmission line.

A device can be understood here as an electrical appliance which processes sensors signals and, in accordance with these, outputs control signals and/or data signals. The device can have an interface which can be embodied in terms of hardware and/or software. In the case of an embodiment in terms of hardware, the interfaces can be, for example, part of a so-called system ASIC, which contains very different functions of the device. However, it is also possible for the interfaces to be dedicated integrated circuits or at least partly consist of discrete components. In the case of an embodiment in terms of software, the interfaces can be software modules which, for example, are present on a microcontroller in addition to other software modules.

In an advantageous embodiment, an injection process, in which a fluid is injected by means of an injection appliance, is determined by the device. In this connection, the device can be designed, for example, to apply electrical signals to a helical spring designed as a coil, to use sensor signals representing an interactivity value such as electrical voltages or currents, and to supply a determination signal. Using the determination signal, information concerning the determination signal is displayed and, in addition or alternatively, stored.

According to one embodiment, the device can have an electrical detection circuit which can comprise at least one energy supply device, a microcontroller and at least one capacitor, a phase-locked loop, a bridge circuit and, in addition or alternatively, an operational amplifier. Such an embodiment affords the advantage that the detection of the inductance value can be carried out reliably and, in terms of a detection principle, can be adapted to special application fields or embodiments of the injection appliance.

The device can also comprise a transmission device for wireless transmission of the determination signal to an appliance outside the injection appliance, a timer device for determining a time point of the injection process, and, in addition or alternatively, a memory for storing the determination signal. Such an embodiment affords the advantage that the injection process can be accurately and reliably recorded and documented inside and, in addition or alternatively, outside the injection appliance.

Moreover, the device can be arranged on a circuit carrier or distributed on a plurality of circuit carriers. In this connection, part of the device can be arranged on a first circuit carrier, and a further part of the device can be arranged on a second circuit carrier, wherein the first circuit carrier can be arranged inside the injection appliance, and wherein the second circuit carrier can be arranged outside the injection appliance, for example in an appliance outside the injection appliance. Such an embodiment affords the advantage that the device can be embodied so as to be easily and cost-effectively adaptable to a predefined appliance geometry.

An injection appliance for injecting fluid is also proposed, wherein the injection appliance has the following features:

a dosing wheel for preselecting a dose quantity of the fluid to be injected in an injection process, wherein the dosing wheel is rotatable about a rotation angle, wherein a set rotation angle of the dosing wheel corresponds to a dose quantity of the fluid that is preselected for the injection process;

at least one helical spring coupled to the dosing wheel for storing potential energy for the injection process, wherein a number of windings of the at least one helical spring is dependent on the set rotation angle of the dosing wheel; and an embodiment of the abovementioned device, wherein the device and the at least one helical spring can be or are connected electrically to each other.

In conjunction with the injection appliance, an embodiment of the abovementioned device can advantageously be used in order to determine an injection process.

According to one embodiment, the injection appliance can have a helical spring which, at a first end, can be or is connected electrically to the device and, at a second end, can be or is connected electrically to the device via an electrically conductive portion of a housing of the injection appliance. In this case, the helical spring can be or is arranged inside the housing and has a plurality of windings with a first diameter and, at the second end, at least one winding with a second diameter which is greater than the first diameter. The at least one winding with a second diameter can be connectable or connected electrically to the electrically conductive portion of the housing. Alternatively, the helical spring can be or is arranged outside the housing. Such an embodiment affords the advantage that an electrical attachment of the helical spring to the device can be realized in a cost-effective manner by using a portion of the housing as return conductor.

Alternatively, the injection appliance can comprise a first helical spring and a second helical spring which, at first ends, can be or are connected electrically to the device and, at second ends, can be or are connected electrically to each other or via an electrically conductive portion of a housing of the injection appliance. In this case, the first helical spring can be or is arranged radially to the outside in relation to the second helical spring. Moreover, the first helical spring and the second helical spring can have a winding direction opposite to each other. Moreover, a diameter of a spring wire of the second helical spring can be smaller than a diameter of a spring wire of the first helical spring. Such an embodiment affords the advantage that modifications to an existing appliance design can be minimized and, therefore, the injection appliance can be realized inexpensively.

In particular, the device can be arranged in the dosing wheel, outside the dosing wheel in the injection appliance, and, in addition or alternatively, in an appliance outside the injection appliance. Such an embodiment affords the advantage that the device can be accommodated cost-effectively and in a way that is easily adaptable to a predefined housing geometry. In other words, electronics for detecting measurement data and for optional communication or dose display can be arranged either in the body of the injection appliance, in a cap for the injection appliance, or in an external appliance.

Moreover, the injection appliance can comprise a display device for displaying the determined injection process using the determination signal from the device. In this case, the display device can be or is connected to the device in such a way as to be able to transmit signals. The display device can be arranged on the dosing wheel, in particular on an end face or front face of the dosing wheel. Such an embodiment affords the advantage that the safety and comfort of the user of the injection appliance can be enhanced, since the information of the determination signal can be displayed directly on the injection appliance.

According to one embodiment, a sensor arrangement for detecting an actually injected quantity of fluid can comprise a spring, in particular a helical spring. During a dosing process of the injection appliance, the spring can be tensioned or rotated about a set rotation angle of the dosing wheel, wherein its number of windings can increase. In this way, the inductance of the spring can change and the set dose can be calculated from this. The value of the quantity or dose can be stored and shown on a for example integrated display of the injection appliance and, in addition or alternatively, can be transmitted to an external appliance.

Also of advantage is a computer program product or computer program with program code, which can be stored on a machine-readable support or storage medium such as a semiconductor memory, a hard disk drive memory or an optical memory and which is used to carry out and/or control the steps of the method according to one of the embodiments described above, in particular when the program product or program is run on a computer or a device.

BRIEF DESCRIPTION OF THE DRAWINGS

Illustrative embodiments of the approach proposed here are explained in more detail in the following description and are shown in the drawings, in which.

DETAILED DESCRIPTION

Before discussing illustrative embodiments below, the background and principles are first of all explained in brief. Generally, there are two customary embodiment variants of injection appliances designed as insulin pens and of their dosing wheel or dosing knob.

In a first embodiment variant, the dosing knob not only performs a rotation movement but also a translation movement. The greater the rotation angle that is set, the farther the dosing knob is rotated out of a housing of the injection appliance via a thread. A distance between dosing knob and housing then corresponds to a path length by which an insulin cartridge is emptied when pressure is applied to the dosing knob, optionally scaled with a transmission ratio factor. For this purpose, a plunger presses onto the cartridge or carpule or ampule. This plunger is arranged at the end of a further threaded rod, which can be rotated only in one direction by means of a locking mechanism. A further mechanical component, for example a driver, ensures that the dosing knob can be rotated outward at most to an extent corresponding to the filling level remaining in the ampule.

In a second embodiment variant, the dosing knob performs only a rotation movement. In this case, although the dosing knob is rotatable, its distance from the housing does not change. A spring, for example, is tensioned by the rotation movement and, during an injection process, a mechanism converts the potential energy of said spring into a translation movement of the plunger.

Persons with diabetes, for example, often consider it a plus if, in an insulin pen, a last administered insulin dose can be continuously detected with the corresponding injection time. For this purpose, a sensor system is required which is able to detect the filling level of the ampule or else the injected dose and can either show it directly in a display on the appliance or can transmit it to an additional appliance. Some sensor designs are based, for example, on resistance measurements and require spring contacts which may possibly become mechanically worn or may exhibit hysteresis. As an alternative to this, there is an optical method, for example, in which one or more light sources are arranged on one side of the carpule and, for example, a CCD line scan camera (CCD=charge-coupled device) is arranged on the opposite side of the carpule. By means of a spatially resolved intensity measurement, this arrangement can be used to draw conclusions regarding the filling level and therefore also the last dose, wherein there is sensitivity to contamination in the optical path. Moreover, magnetic detection methods are also known in which a ring magnet is rotated via a Hall effect sensor.

In the following description of expedient illustrative embodiments of the present disclosure, the elements shown in the various figures and having similar effects are designated by the same or similar reference signs, thereby avoiding repeated description of these elements.

Figure 1:
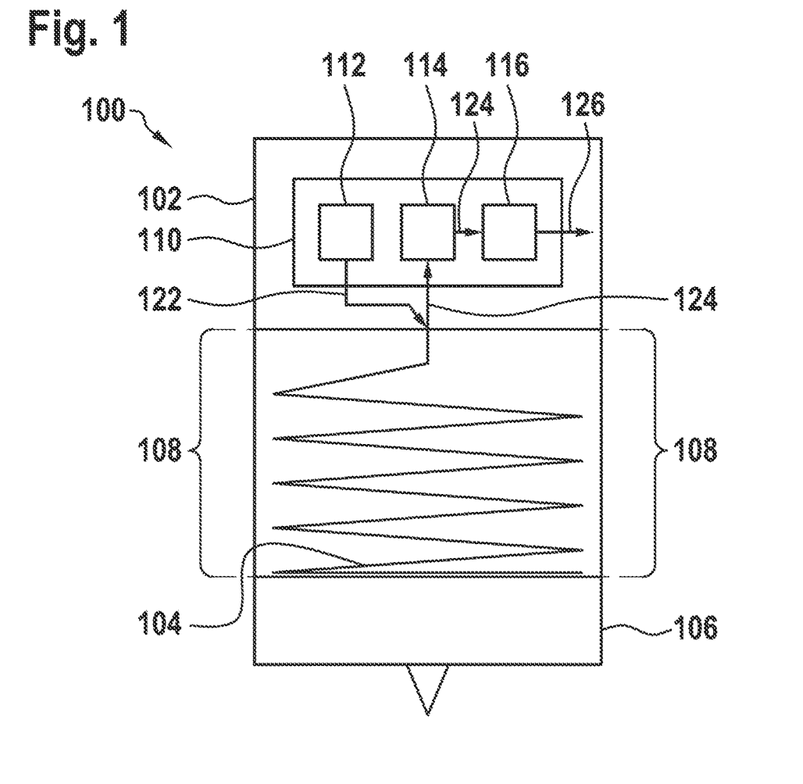
FIG. 1 shows a schematic view of an injection appliance with a device according to an illustrative embodiment.

FIG. 1 shows a schematic view of an injection appliance 100 with a device 110 according to an illustrative embodiment. The injection appliance 100 is designed to inject a fluid in an injection process. For example, the injection appliance 100 is an insulin pen for injection of insulin.

Of the injection appliance 100 according to the illustrative embodiment in FIG. 1, the view of FIG. 1 depicts only a dosing wheel 102 or dosing knob 102, a helical spring 104, a shaft 106 or housing 106 with at least one electrically conductive portion 108, and a determination device 110 for determining an injection process of the injection appliance 100.

The dosing wheel 102 is arranged to be rotatable about a rotation angle. The dosing wheel 102 is designed to permit a preselection of a dose quantity of the fluid that is to be injected in the injection process. Here, a set rotation angle of the dosing wheel 102 corresponds to a dose quantity of the fluid that is preselected for the injection process.

The helical spring 104 is mechanically coupled to the dosing wheel 102. By means of the helical spring 104, potential energy can be stored for the injection process. The helical spring 104 has a number of windings that is dependent on the set rotation angle or on a rotation movement of the dosing wheel 102.

According to the illustrative embodiment shown in FIG. 1, the determination device 110 is arranged in the dosing wheel 102. Here, the determination device 110 is connected electrically to the helical spring 104. According to another illustrative embodiment, the determination device 110 can be arranged outside the dosing wheel 102 in the injection appliance 100. According to a further illustrative embodiment, at least part of the determination device 110 can be arranged in an appliance outside the injection appliance 100.

The determination device 110 has an applicator device 112, a detection device 114 or electrical detection circuit 114 and a supply device 116. The applicator device 112 is designed to apply an electrical signal 122 or excitation signal 122 to the helical spring 104. The excitation signal 122 is, for example, an electrical alternating voltage or direct voltage. The detection device 114 is designed to detect an inductance value 124 of the helical spring 104. In the detection of the inductance value 124, the number of windings of the helical spring 104 is variable and dependent on the set rotation angle of the dosing wheel 102. Thus, the inductance value 124 changes with the number of windings of the helical spring 104 or the set angle of the dosing wheel 102. The supply device 116 is designed to use the detected inductance value 124 to supply a determination signal 126 which represents the determined injection process of the injection appliance 100.

According to the illustrative embodiment shown in FIG. 1, the determination device 110 or electronic system is accommodated or arranged in the dosing knob 102. Here, the helical spring 104 is electrically connected at a first end, or on one side, to the determination device 110. For contacting a second end, or the other side, of the helical spring 104, the shaft 106 of the injection appliance 100 has the electrically conductive portion 108 for example in the form of an electrically conductive coating of a housing wall. In this way, a return conductor is provided for the helical spring 104 through the housing 106. A contacting between helical spring 104 and electrically conductive portion 108 or housing wall is realized, for example, by a spring contact. For this purpose, at least one winding of the helical spring 104 directed farthest away from the dosing knob 102 is designed, for example, with a diameter that permits contact with the electrically conductive portion 108.

Figure 2:
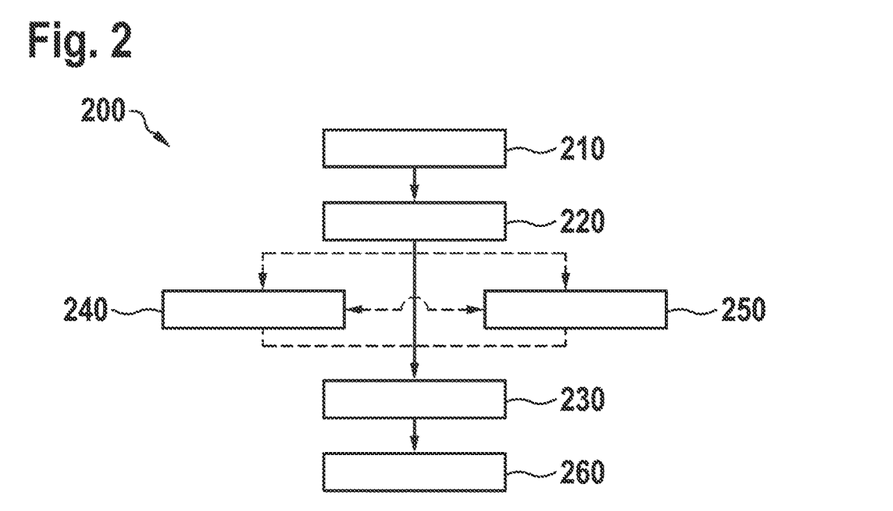
FIG. 2 shows a flow chart of a method for determining according to an illustrative embodiment.

FIG. 2 shows a flow chart of a method 200 for determination according to one illustrative embodiment. The method 200 for determination can be carried out to determine an injection process of an injection appliance by means of which a fluid is injected. In the injection process, for example, a dose of insulin can be injected into a living being, in particular a human, by means of an insulin pen. The method 200 for determination can in this case be carried out in conjunction with, or using, an injection appliance from FIG. 1 or a similar injection appliance. To be more exact, the method 200 for determination can be carried out by means of the device from FIG. 1 or a similar device.

The method 200 for determination has a step 210 in which an electrical signal is applied to at least one helical spring of the injection appliance coupled to a dosing wheel of the injection appliance. Then, in a detection step 220, an inductance value of the at least one helical spring is detected. The at least one helical spring has a number of windings that is dependent on a set rotation angle of the dosing wheel. The set rotation angle corresponds to a dose quantity of the fluid that is preselected for the injection process. In a subsequent step 230, a determination signal is supplied using the inductance value detected in detection step 220.

According to one illustrative embodiment, the method 200 for determination also has a calculating or determining step 240 and/or a combining step 250. In this case, the calculating step 240 and/or the combining step 250 can be carried out, for example, between the detection step 220 and the supply step 230. In the calculating step 240, the dose quantity of the fluid is calculated using the detected inductance value. In the combining step 250, the inductance value detected in the detection step 220 or the dose quantity calculated in the calculating step 240 is combined with a time stamp which represent a time point of the injection process. Then, in the supply step 230, a determination signal is supplied which represents the dose quantity calculated in the calculating step 240 and/or the time point of the injection process combined in the combining step 250.

According to one illustrative embodiment, the determination method 200 moreover has a step 260 in which the determination signal is output. In the output step 260, the determination signal is output to an interface to a transmission device for transmitting the determination signal to an appliance outside the injection appliance, to an interface to a memory inside or outside the injection appliance, and/or to an interface to a display device of the injection appliance.

Figure 3:
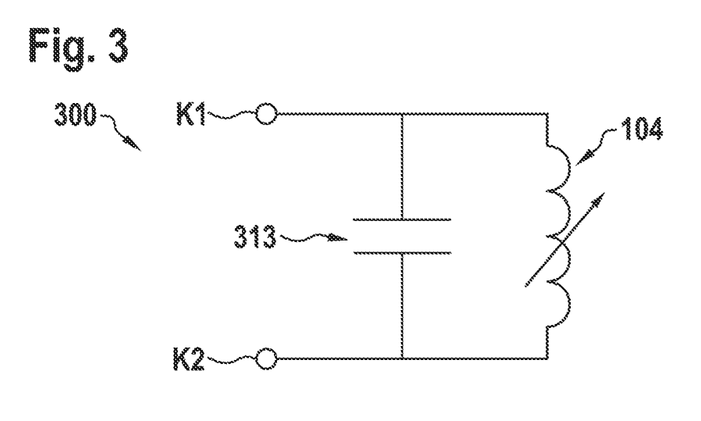
FIG. 3 shows a schematic view of a resonant circuit for an injection appliance according to an illustrative embodiment.

FIG. 3 shows a schematic view of an electrical resonant circuit 300 for an injection appliance according to an illustrative embodiment. The resonant circuit 300 can in this case be used for the injection appliance of FIG. 1 or a similar injection appliance. The resonant circuit 300 according to the illustrative embodiment shown in FIG. 3 has a coil with variable inductance L in the form of the helical spring 104 and a capacitor 313 with a capacitance C. The capacitor can in this case be part of the determination device from FIG. 1 or of a similar determination device. The helical spring 104 or the coil and the capacitor 313 are here electrically connected in parallel between a first contact K1 and a second contact K2 of the resonant circuit 300.

As regards a measurement principle or detection principle of an inductance value of the helical spring 104 which functions as a coil, its inductance L or inductance value is obtained according to the following calculation rule:

$$L = \mu_0 \frac{N^2 A}{l}$$

Here, $\mu_0$ is the magnetic field constant, N is a number of windings of the helical spring 104, A is the cross-sectional surface area of the helical spring 104, and l is a coil length or the length of the helical spring 104. During a rotation of the helical spring 104, all the parameters except for the number of windings N remain more or less constant, giving a quadratically increasing inductance increase. Taking examples of coil dimensions, for example a length of the helical spring 104 of 5 cm in the relaxed state, a number of windings of 30 and a diameter of 1 cm, this gives inductance values ranging from a few hundred nH to several μH.

If the helical spring 104 or coil is connected in the electrical resonant circuit 300 of FIG. 3, this gives a resonance frequency f which depends on the inductance L, i.e. the number of windings N, according to the following calculation rule:

$$f = \frac{1}{2\pi\sqrt{LC}}$$

For example, if a capacitor with a capacitance of 500 pF is used, the resonance frequency f lies in the range of a few MHz. Assuming 20 dose values per rotation of the dosing knob of the injection appliance, this therefore gives a sensitivity, for example, of about 10 kHz frequency change per dose unit. This is measurable by means of available microcontrollers.

According to other illustrative embodiments, in a departure from measuring the resonance frequency, it is alternatively possible to determine the inductance using, for example, the measurement principles mentioned below. For example, an L integrator can be used, in which case a direct voltage is applied to the helical spring 104 and the increasing current is converted by an operational amplifier into a measurement voltage, which is measured and allows conclusions to be drawn concerning the inductance. Alternatively, a DC-DC converter (direct current, direct voltage, direct signal) can be used, in which case energy of the helical spring 104 or measuring coil is charged on a capacitor whose voltage serves as measurement signal. Moreover, determination of the shunt resistance can alternatively be carried out, in which case, for example, a commercially available chip can be used which is designed to determine an effective resonant shunt resistance and a resonance frequency of a resonant circuit, in which case the resonance frequency can be set by selecting a suitable shunt capacitance. Moreover, a reactive voltage divider can alternatively be used, in which case, for example, a phase relationship between an exciting sinus signal and a voltage across an LC resonant circuit is determined via a phase-locked loop (PLL), and the inductance is then calculated from the phase. Alternatively, the helical spring 104 or measuring coil can also be integrated in a bridge circuit, in which case a demodulation of a measurement signal takes place and, for example, at least one second coil or a reference coil is provided.

Figure 4:
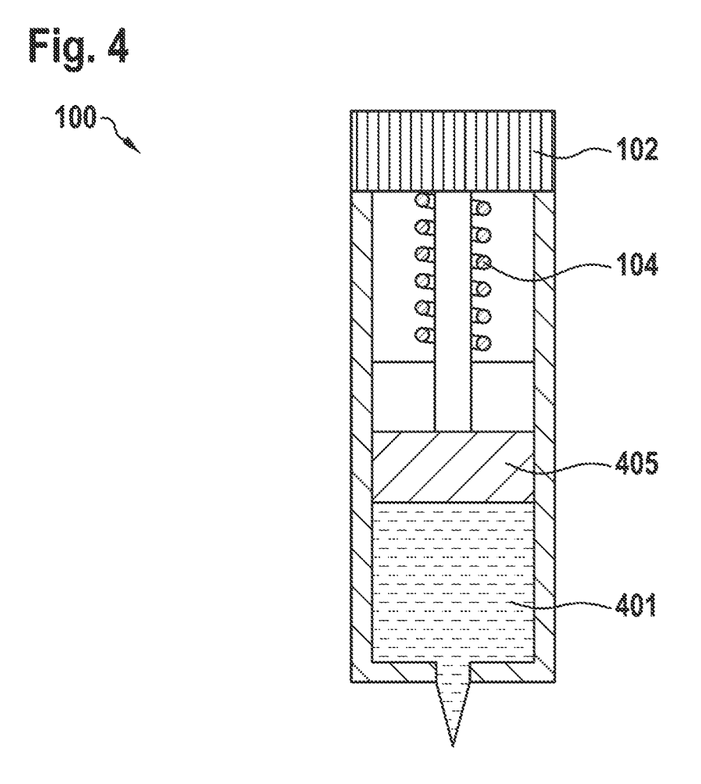
FIG. 4 shows a schematic view of an injection appliance according to an illustrative embodiment.

FIG. 4 shows a schematic view of an injection appliance 100 according to an illustrative embodiment. The injection appliance 100 is in this case designed as an injection pen or insulin pen. The injection appliance 100 corresponds to or is similar to the injection appliance from FIG. 1. Of the injection appliance 100 in FIG. 4, the view shows the dosing wheel 102, the helical spring 104, a fluid 401 or an injection liquid 401, and a plunger 405. In this case, the helical spring 104 is integrated inside the injection appliance 100 or inside a housing of the injection appliance 100.

To put it another way, FIG. 4 shows in a simplified view a structure of an injection appliance 100 according to an illustrative embodiment in the form of what is called a smart pen. The figure does not depict optional mechanical components which are designed to convert a rotation of the helical spring 104 during an injection process into a translation movement of the plunger 405.

Figure 5:
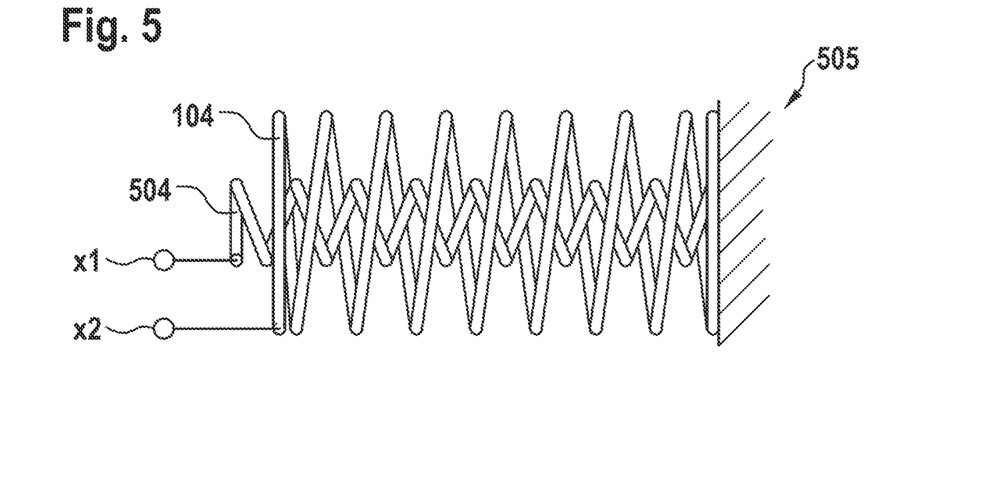
FIG. 5 shows a schematic and partially perspective view of a helical spring assembly for an injection appliance according to an illustrative embodiment.

FIG. 5 shows a schematic and partially perspective view of a helical spring assembly for an injection appliance according to an illustrative embodiment. The helical spring assembly can in this case be used for the injection appliance from FIG. 1 or for a similar injection appliance.

The helical spring assembly has a first helical spring 104 and a second helical spring 504. Here, the second helical spring 504 is arranged inside the first helical spring 104. The second helical spring 504 has a smaller diameter than the first helical spring 104 and, on a side directed toward a feed-through element 505 of the injection appliance, is electrically connected to the first helical spring 104. Alternatively, a surface of the feed-through element 505 102 can be coated or configured to be electrically conductive. A winding direction of the first helical spring 104 is counter to that of the second helical spring 504, such that a magnetic field can be built up. Moreover, a diameter of a spring wire of the second helical spring 504, the inner spring, is optionally smaller than a diameter of a spring wire of the first helical spring 104, the outer spring, such that second helical spring 504 functioning as return conductor has only a minimal influence on the mechanical properties of the first helical spring 104.

Thus, electrical contact of the first helical spring 104 is realized by means of the second helical spring 504. The helical spring assembly has a first connection x1 and a second connection x2. Here, for example, the first connection x1 is arranged on an end of the second helical spring 504 directed away from the feed-through element 505, and the second connection x2 is arranged on an end of the first helical spring 104 directed away from the feed-through element 505. The connections x1 and x2 are electrically connectable to a determination device accommodated, for example, in the dosing knob of the injection appliance.

Figure 6:
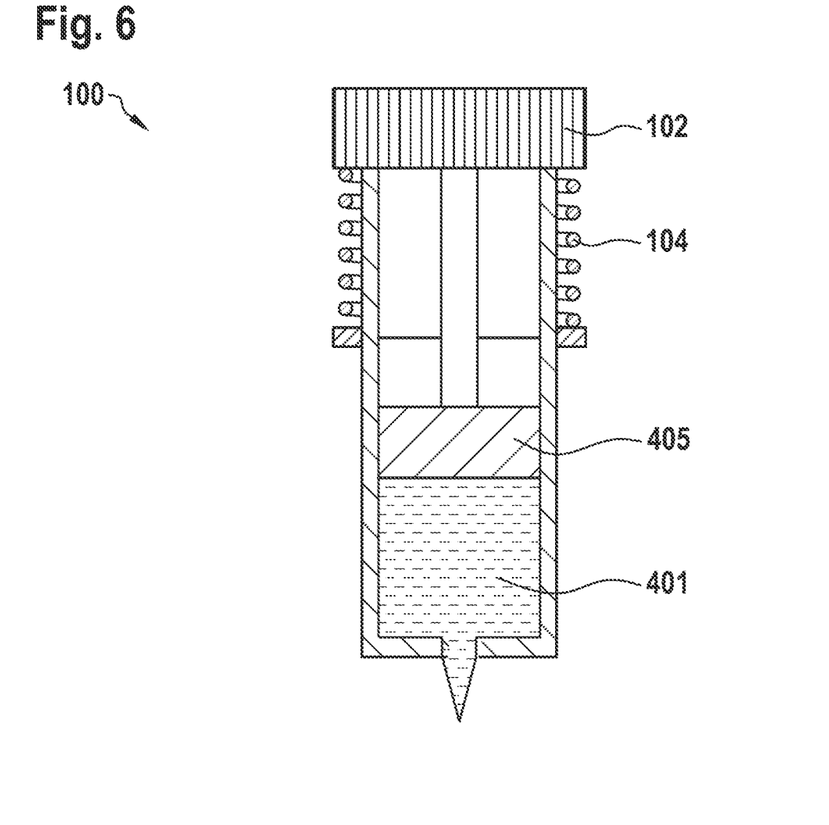
FIG. 6 shows a schematic view of an injection appliance according to an illustrative embodiment.

FIG. 6 shows a schematic view of an injection appliance 100 according to an illustrative embodiment. The injection appliance 100 in this case corresponds to the injection appliance from FIG. 4, except that the helical spring 104 is arranged outside a housing or shaft or the injection appliance 100.

In this case, the helical spring 104 is arranged outside a body of the injection appliance 100, and an inner structure of the injection appliance 100 does not have to be modified or has to be modified only to a minimum extent. In other words, the helical spring 104 is in this case integrated outside the injection pen. The helical spring 104 is in this case attached as an external element and surrounds the shaft of the injection appliance 100. By means of rigid coupling to the rotatably mounted dosing knob 102, the helical spring 104 is rotated during dose adjustment and its number of windings or its inductance value increases.

Figure 7:
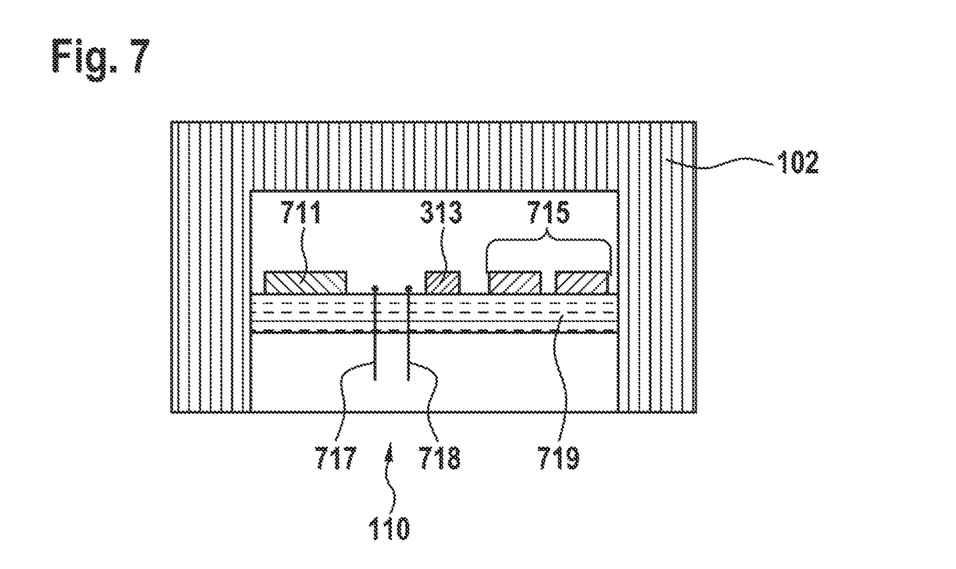
FIG. 7 shows a schematic view of a dosing wheel for an injection appliance with a device according to an illustrative embodiment.

FIG. 7 shows a schematic view of a dosing wheel 102 for an injection appliance with a device 110 according to an illustrative embodiment. The dosing wheel 102 is the dosing wheel of the injection appliance from FIG. 1, FIG. 4 or FIG. 6 or a similar dosing wheel. The device 110 or determination device 110 corresponds to or is similar to the determination device from FIG. 1. The device 110 can also use the resonant circuit from FIG. 3 or a similar resonant circuit.

Of the determination device 110 according to the illustrative embodiment depicted here, the view of FIG. 7 shows a capacitor 313, an energy supply device 711, add-on components 715 or further components 715, electrical connections 717 and 718 for the at least one helical spring, and a substrate 719 or circuit carrier 719.

According to the illustrative embodiment shown in FIG. 7, the determination device 110 or electronic components thereof for detecting the inductance, for calculating the dose and for transmitting the data, are arranged on the substrate 719 inside the dosing knob 102.

FIG. 7 shows schematically the two connections 717 and 718 of the helical spring, the capacitor 313 for measuring the inductance via the resonance frequency of a resonant circuit, the energy supply device 711, which can be designed e.g. as a button cell or another energy store, and also the add-on components 715. The add-on components 715 have, for example, at least one microcontroller for measuring the resonance frequency and for calculating the dose, and a unit for wireless transmission of the inductance value or of the determination signal, e.g. via Bluetooth or NFC (near field communication).

Figure 8:
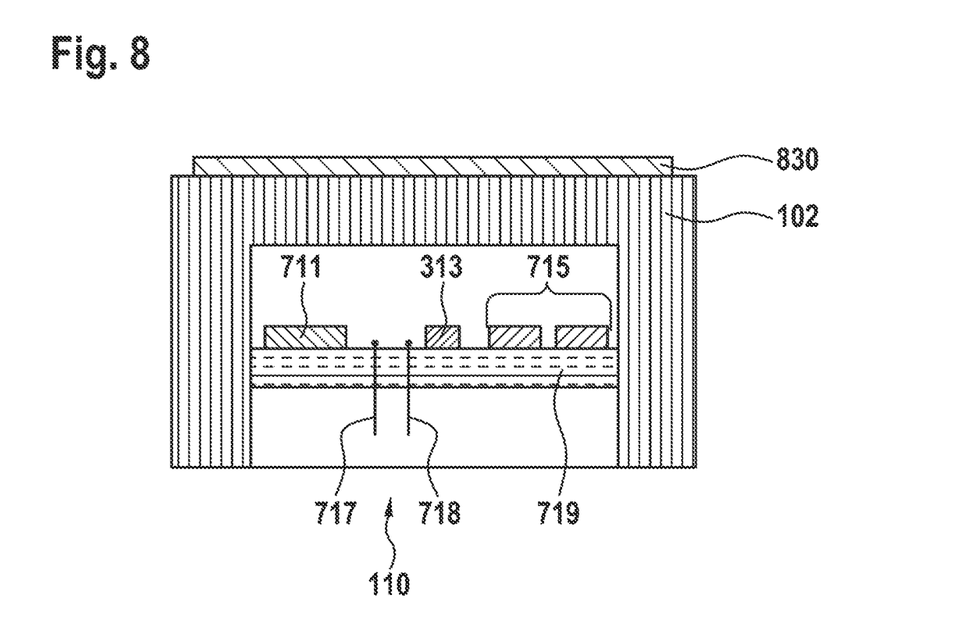
FIG. 8 shows a schematic view of a dosing wheel for an injection appliance with a device according to an illustrative embodiment.

FIG. 8 shows a schematic view of a dosing wheel 102 for an injection appliance with a device 110 according to an illustrative embodiment. Here, the dosing wheel 102 and the device 110 correspond to the dosing wheel and the device of FIG. 7, except that, according to the illustrative embodiment shown in FIG. 8, a display device 830 is additionally arranged on the dosing wheel 102. Here, the display device 830 is connected to the determination device 110 in such a way as to be able to transmit signals. The display device 830 is designed to display the determined injection process, in particular an injected dose of the fluid and a time point of the injection process, using the determination signal from the determination device 110.

To put it another way, in the illustrative embodiment shown in FIG. 8, the display device 830 is integrated in the dosing knob 102. In this case, information concerning the determined injection process can be displayed by means of the display device 830. Here, the display device 830 is arranged on a front face or end face of the dosing knob 102. The display device 830 is designed, for example, as an E-ink display which permits continuous, low-energy display. In addition, a timing device can be part of the determination device 110 or of the injection appliance. The time detection device can be part, for example, of the microcontroller and can be initialized on first radio contact.

Referring to FIGS. 1 to 8, it should be noted that, as an alternative to integrating the determination device 110 in the dosing knob 102, it is also conceivable for the determination device 110 to be arranged on the shaft 106 of the injection appliance 100 or in an external housing. In this case, for example, it is possible for only the resonant circuit 300 to be arranged in the injection appliance 100, and its resonance frequency can be measured, e.g. wirelessly, by means of the external appliance.

If an illustrative embodiment comprises an "and/or" link between a first feature and a second feature, this should be interpreted as meaning that the illustrative embodiment has both the first feature and the second feature in accordance with one embodiment and either only the first feature or only the second feature in accordance with a further embodiment.

What is claimed is:

1. An injection appliance for injecting a fluid, comprising:
    a dosing wheel configured to preselect a dose quantity of the fluid to be injected in an injection process, the dosing wheel rotatable about a rotation angle, and a set rotation angle of the dosing wheel corresponds to a preselected dose quantity of the fluid that is preselected for the injection process;
    at least one helical spring coupled to the dosing wheel and configured to store potential energy for the injection process, a number of windings of the at least one helical spring dependent on the set rotation angle of the dosing wheel; and
    a device configured to determine the injection process including (i) a voltage source configured to apply an electrical signal to the at least one helical spring, (ii) a sensor configured to detect an inductance value of the at least one helical spring, and (iii) a signal generator configured to generate a determination signal representing the determined injection process using the detected inductance value,
    wherein the device and the at least one helical spring are connected electrically.

2. The injection appliance according to claim 1, wherein the device is located in the dosing wheel, outside the dosing wheel in the injection appliance, or in an appliance outside the injection appliance.

3. The injection appliance according to claim 1, further comprising:
    a display device configured to display the determined injection process using the determination signal, the display device connected to the device in such a way as to be able to transmit signals.

4. The injection appliance according to claim 1, wherein:
    the at least one helical spring, at a first end, is connected electrically to the device and, at a second end, is connected electrically to the device via an electrically conductive portion of a housing of the injection appliance, and
    the at least one helical spring includes a plurality of windings with a first diameter and, at the second end, at least one winding with a second diameter which is greater than the first diameter.

5. The injection appliance according to claim 4, wherein the at least one helical spring is a first helical spring and the injection appliance further comprises:
    a second helical spring,
    wherein the second helical spring, at a first end, is connected electrically to the device and, at a second end, is connected electrically to the first helical spring or to an electrically conductive portion of a housing of the injection appliance,
    wherein the first helical spring is arranged radially outside in relation to the second helical spring.

* * * * *